United States Patent
Ueda et al.

(10) Patent No.: US 7,184,823 B2
(45) Date of Patent: Feb. 27, 2007

(54) BODY COMPOSITION MANAGEMENT APPARATUS FOR PREGNANT WOMAN

(75) Inventors: Yasuo Ueda, Sasayama (JP); Motoyoshi Maruo, Haibara-cho (JP); Yoshihiko Ashitaka, Ashiya (JP); Yuka Honda, Tokyo (JP)

(73) Assignee: Tanita Corporation, Tokyo (JP)

( * ) Notice: Subject to any disclaimer, the term of this patent is extended or adjusted under 35 U.S.C. 154(b) by 140 days.

(21) Appl. No.: 10/855,531

(22) Filed: May 28, 2004

(65) Prior Publication Data

US 2004/0243020 A1    Dec. 2, 2004

(30) Foreign Application Priority Data

May 30, 2003    (JP)    ............................. 2003-154218

(51) Int. Cl.
*A61B 5/05*    (2006.01)

(52) U.S. Cl. .................................................. 600/547

(58) Field of Classification Search ............... 600/300, 600/304, 547, 551, 587, 591
See application file for complete search history.

(56) References Cited

U.S. PATENT DOCUMENTS 6,434,422 B1 * 8/2002 Tomoda et al. ............. 600/547
6,643,542 B1 * 11/2003 Kawanishi .................. 600/547
6,679,854 B2    1/2004 Honda et al.
2003/0023186 A1    1/2003 Ueda et al.

FOREIGN PATENT DOCUMENTS

| EP | 1 080 687 A1 | 3/2001 |
| EP | 1 279 367 A1 | 1/2003 |
| JP | P2002-200086 A | 7/2002 |
| JP | P2003-33356 A | 2/2003 |
| JP | P2003-102696 A | 4/2003 |

* cited by examiner

*Primary Examiner*—Max Hindenburg
*Assistant Examiner*—Jonathan Foreman
(74) *Attorney, Agent, or Firm*—McDermott Will & Emery LLP

(57) ABSTRACT

A body composition management apparatus for a pregnant woman which measures body fat or body water by a bioelectrical impedance method is provided. The apparatus comprises: first input means, second input means, measurement means, first computation means, and second computation means, wherein the first input means inputs personal data of a pregnant woman such as a body height and a body weight, the second input means inputs the gestational weeks, the measurement means measures the bioelectrical impedance of the pregnant woman, the first computation means computes a body fat mass or a total body water from the personal data and the impedance, and the second computation means computes a body fat mass or total body water in a non-pregnant state from the computed body fat mass or total body water and the amount of an increase in body weight from the non-pregnant state.

3 Claims, 10 Drawing Sheets

| DATE AND TIME OF MEASUREMENT : 6/1/2001 10:27 AM | | |
|---|---|---|
| SEX AND BODY TYPE MODE | | MATERNITY |
| GESTATIONAL WEEKS | | 24 WEEKS AND 5 DAYS |
| AGE | | 35 |
| BODY HEIGHT | | 159.0cm |
| BODY WEIGHT BEFORE AND AFTER CORRECTION | 54.0kg | 52.0kg |
| BODY WEIGHT OF FETUS | | 1.201kg |
| WEIGHT OF AMNIOTIC FLUID | | 0.534kg |
| WEIGHT OF PLACENTA | | 0.265kg |
| IMPEDANCE | | 580Ω |
| BODY FAT PERCENTAGE | | 21.3% |
| BODY FAT MASS | | 11.1kg |
| FAT FREE MASS | | 40.9kg |
| TOTAL BODY WATER | | 29.9kg |
| BMI BEFORE CORRECTION | | 21.4 |
| BODY WEIGHT BEFORE PREGNANCY | | 49.0kg |
| BODY FAT MASS BEFORE PREGNANCY | | 9.2kg |
| BODY WATER CONTENT BEFORE PREGNANCY | | 28.0kg |
| AMOUNT OF INCREASE IN BODY WEIGHT FROM NON-PREGNANT STATE | | 5.0kg |
| AMOUNT OF INCREASE IN BODY FAT FROM NON-PREGNANT STATE | | 1.9kg |
| AMOUNT OF INCREASE IN BODY WATER FROM NON-PREGNANT STATE | | 1.9kg |

| DATE AND TIME OF MEASUREMENT : 6/1/2001  10:27 AM | | |
|---|---|---|
| SEX AND BODY TYPE MODE | | NORMAL MALE |
| AGE | | 35 |
| BODY HEIGHT | | 168.0cm |
| BODY WEIGHT | | 63.4kg |
| IMPEDANCE | | 525Ω |
| FAT PERCENTAGE | | 26.2% |
| FAT MASS | | 16.6kg |
| FAT FREE MASS | | 46.8kg |
| TOTAL BODY WATER | | 34.2kg |
| BMI | | 23.9 |

| | | |
|---|---|---|
| DATE AND TIME OF MEASUREMENT : 6/1/2001 10:27 AM | | |
| SEX AND BODY TYPE MODE | | MATERNITY |
| GESTATIONAL WEEKS | | 24 WEEKS AND 5 DAYS |
| AGE | | 35 |
| BODY HEIGHT | | 159.0cm |
| BODY WEIGHT BEFORE AND AFTER CORRECTION | 54.0kg | 52.0kg |
| BODY WEIGHT OF FETUS | | 1.201kg |
| WEIGHT OF AMNIOTIC FLUID | | 0.534kg |
| WEIGHT OF PLACENTA | | 0.265kg |
| IMPEDANCE | | 580Ω |
| BODY FAT PERCENTAGE | | 21.3% |
| BODY FAT MASS | | 11.1kg |
| FAT FREE MASS | | 40.9kg |
| TOTAL BODY WATER | | 29.9kg |
| BMI BEFORE CORRECTION | | 21.4 |
| BODY WEIGHT BEFORE PREGNANCY | | 49.0kg |
| BODY FAT MASS BEFORE PREGNANCY | | 9.2kg |
| BODY WATER CONTENT BEFORE PREGNANCY | | 28.0kg |
| AMOUNT OF INCREASE IN BODY WEIGHT FROM NON-PREGNANT STATE | | 5.0kg |
| AMOUNT OF INCREASE IN BODY FAT FROM NON-PREGNANT STATE | | 1.9kg |
| AMOUNT OF INCREASE IN BODY WATER FROM NON-PREGNANT STATE | | 1.9kg |

BODY COMPOSITION MANAGEMENT APPARATUS FOR PREGNANT WOMAN

BACKGROUND OF THE INVENTION (i) Field of the Invention

The present invention relates to a body composition management apparatus for a pregnant woman which measures the body fat mass or total body water of a pregnant woman.

(ii) Description of the Related Art

It is important to manage a body weight and the amount of an increase in the body weight during pregnancy. Further, body fat or body water for a pregnant woman has received attention, and data in a non-pregnant state, i.e., before pregnancy, and data during pregnancy are input, and a change in body fat mass or total body water during pregnancy is examined.

In the case of conventional apparatuses, data in the non-pregnant state becomes starting data. However, most pregnant women only remember the pre-pregnancy weight (the weight in the non-pregnant state) at most. And they do not remember the pre-pregnancy body fat mass and total body water in many cases.

For this reason, only the body weight and the amount of an increase in the body weight are managed in most cases.

SUMMARY OF THE INVENTION

According to one aspect of the present invention, there is provided a body composition management apparatus for a pregnant woman which measures body fat or body water by a bioelectrical impedance method, the apparatus comprising:
first input means,
second input means,
measurement means,
first computation means, and
second computation means,
wherein
the first input means inputs personal data of a pregnant woman such as a body height and a body weight,
the second input means inputs the gestational weeks,
the measurement means measures the bioelectrical impedance of the pregnant woman,
the first computation means computes a body fat mass or a total body water from the personal data and the impedance, and
the second computation means computes a body fat mass or total body water in a non-pregnant state from the computed body fat mass or total body water and the amount of an increase in body weight from the non-pregnant state.

According to one embodiment of the present invention, the second input means takes in an expected date of birth so as to determine the gestational weeks.

According to one embodiment of the present invention, the apparatus prepares health management data from a change in the body fat mass or total body water between the non-pregnant state and the time of the measurement.

DETAILED DESCRIPTION OF THE PREFERRED EMBODIMENTS

Figure 1:
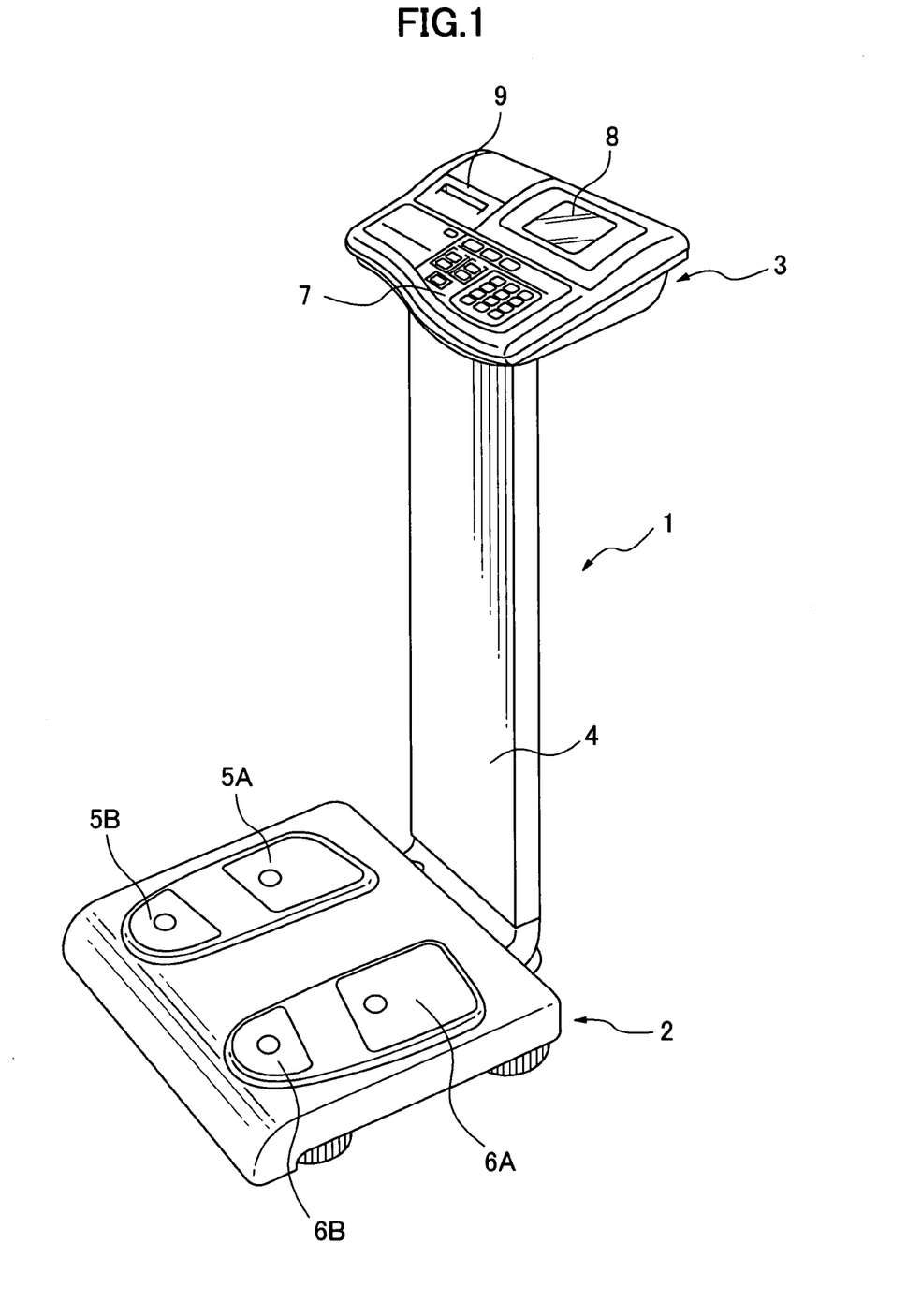
FIG. 1 is an external perspective view of an apparatus according to the present invention.

An embodiment of the present invention will be described by use of the drawings. FIG. 1 is an external perspective view of a body composition management apparatus 1 for a pregnant woman according to the present invention. The apparatus 1 roughly comprises a measuring section 2, a display/printing section 3, and a support post 4 which is fixed to a not-shown bedplate of the measuring section 2 and the display/printing section 3. The measuring section 2 has the same constitution as that of a known body fat meter and has a body weight measuring sensor therein. A subject can measure her body weight by standing on the top surface of the measuring section 2. On the top surface of the measuring section 2, current supplying electrodes 5A and 6A and voltage measuring electrodes 5B and 6B are provided so as to measure a bioelectrical impedance between both feet.

Figure 2:
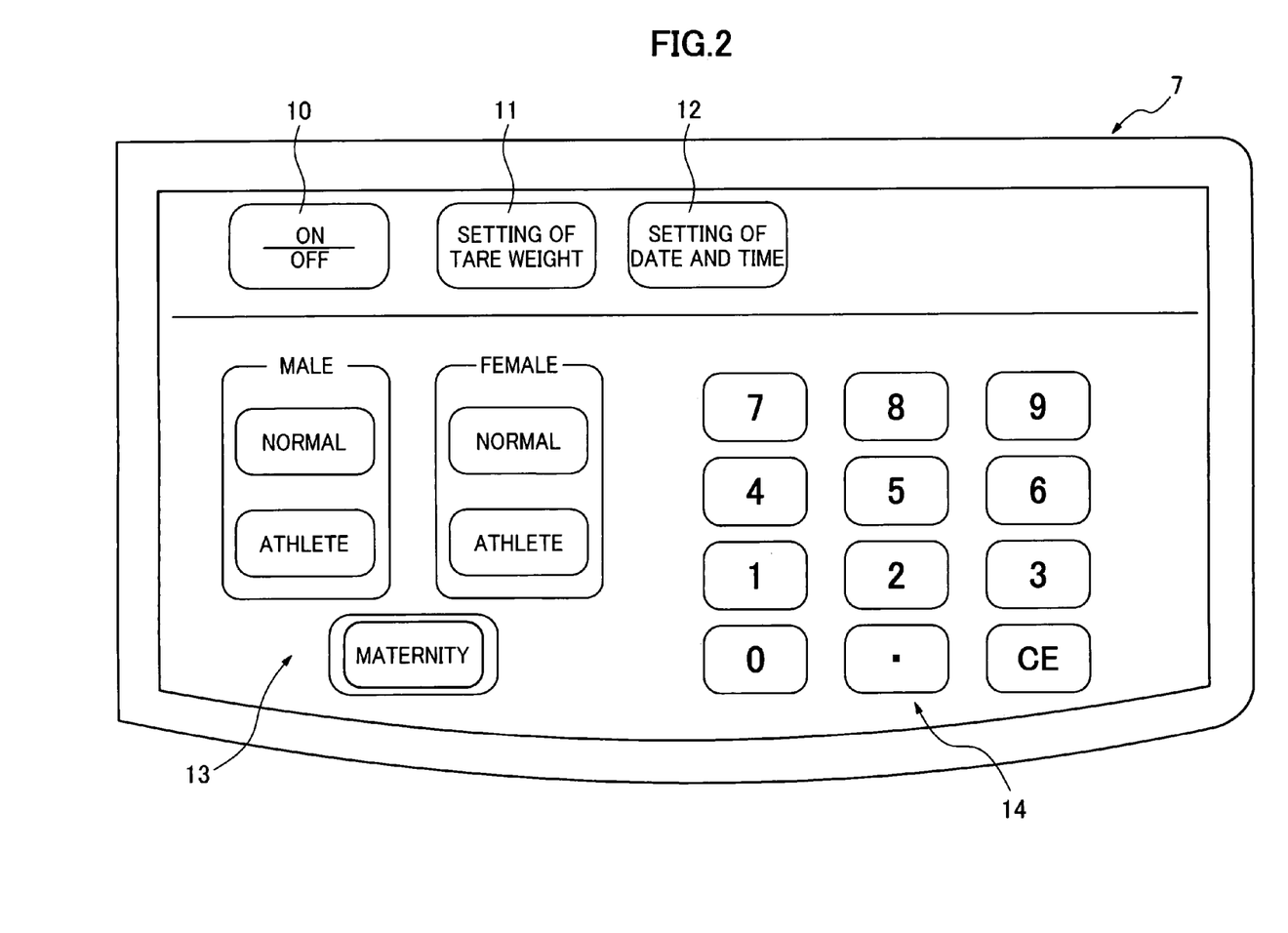
FIG. 2 is a diagram showing a display/printing section in the apparatus according to the present invention.

Meanwhile, the display/printing section 3 comprises an operation section 7, a display section 8 for displaying input data and results, and a printing section 9 for printing the results of measurements, as shown in FIG. 2. The operation section 7 comprises a power switch 10, a tare weight setting key 11 for setting the weight of the tare of a subject, a key 12 for setting a date and a time, keys 13 for setting sex and a body type, and a numeric keypad 14 for setting data and the like.

Figure 3:
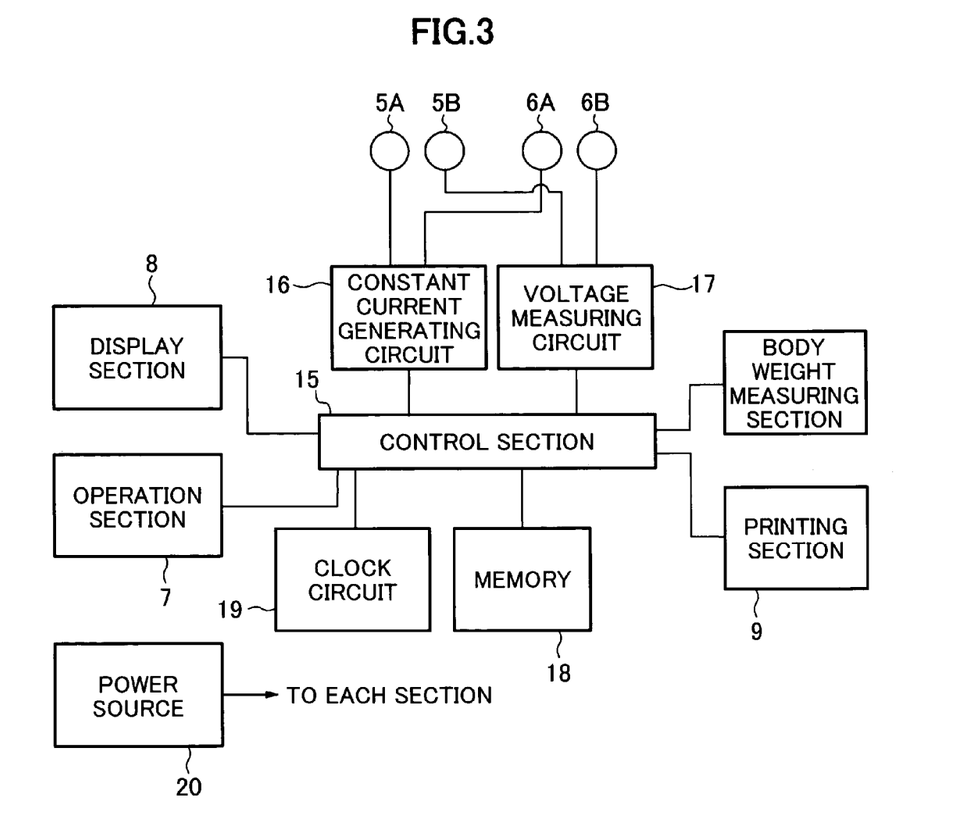
FIG. 3 is an electrical block diagram.

FIG. 3 is a block diagram illustrating electrical connections of the body composition management apparatus 1. The body composition management apparatus 1 has a control section 15 which incorporates a microcomputer. To the control section 15, the switch and keys of the operation section 7 of FIG. 2 are connected, and the display section 8 and the printing section 9 are also connected.

Further, from the measuring section 2, the current supplying electrodes 5A and 6A are connected to the control section 15 via a constant current generating circuit 16, and the voltage measuring electrodes 5B and 6B are connected via a voltage measuring circuit 17. The body weight measuring sensor is also connected to the control section 15.

In addition, a memory 18 for storing data and a clock circuit 19 for generating date and time data such as the gestational weeks (the number of weeks of pregnancy) are also connected to the control section 15. A power source 20 supplies electric power to these components.

Figure 4:
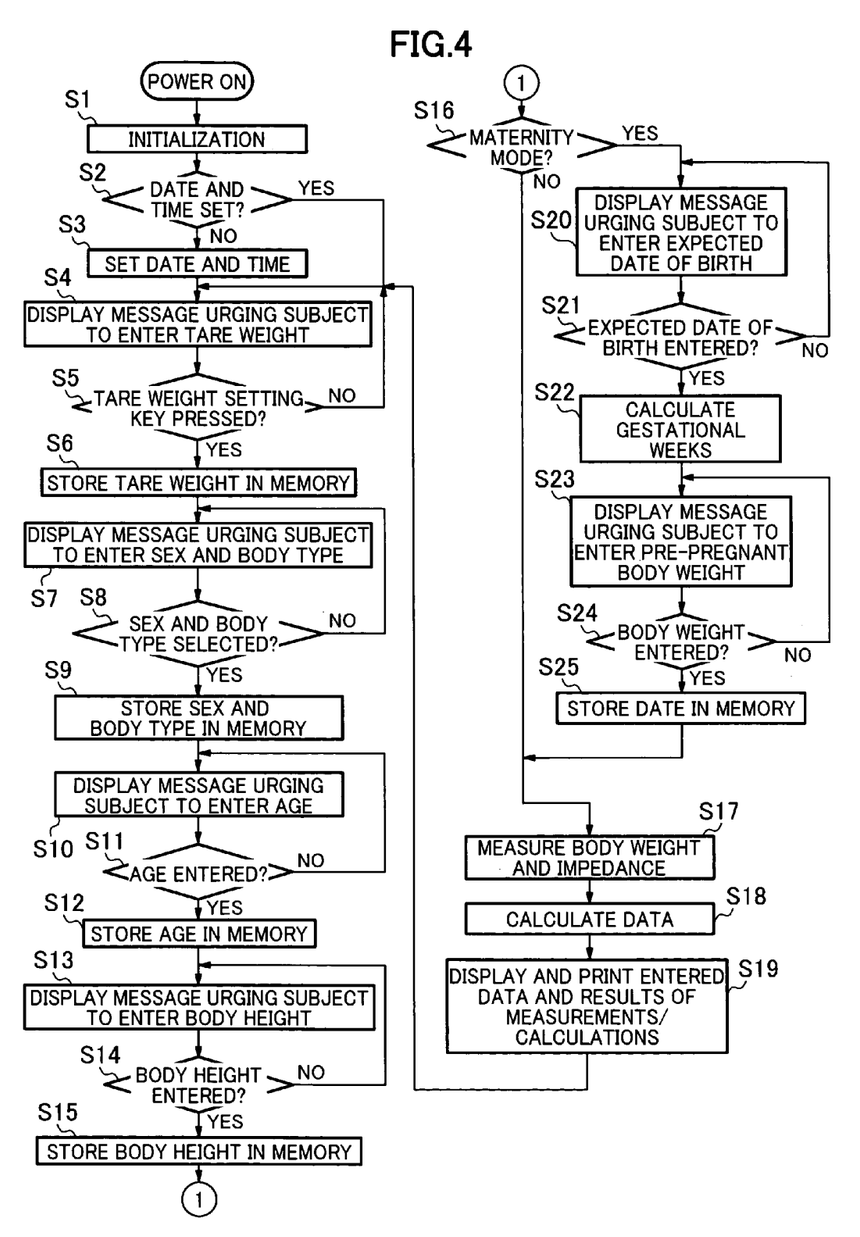
FIG. 4 is a flowchart of the apparatus according to the present invention.

Next, the operation of the body composition management apparatus 1 of the present invention will be described by use of the flowchart of FIG. 4. Firstly, when the power switch 10 is pressed, the control section 15 initializes the microcomputer, the memory 18 and the like in STEP S1. Then, the control section 15 determines in STEP S2 whether a date and a time are already set. If the date and time are already set, the control section 15 proceeds to STEP S4. If the date and time are not set yet, the control section 15 sets the date and time in STEP S3. A detailed description of the setting of the date and time is omitted because it is the same as that used in general apparatuses.

In STEP S4, the control section 15 displays a message "Please enter the weight of your clothing or tare using the numeric keypad 14 and press the tare weight setting key 11 when you are done." in the display section 8. Then, when a subject enters 1.0 kg by use of the numeric keypad 14 and presses the tare weight setting key 11, it is determined to be "Yes" in STEP S5, and the control section 15 proceeds to STEP S6 and stores the tare weight in the memory 18. If the tare weight setting key 11 is not pressed in STEP S5, the control section 15 returns to STEP S4 and repeats displaying the message which urges the subject to enter the tare weight.

Then, in STEP S7, the control section 15 displays in the display section 8 a message which urges the subject to press a key which matches the subject among the keys 13 for setting sex and a body type. For example, when the subject is a normal male, he presses a "normal" key in the frame named "male" of FIG. 2. Then, the control section 15 determines in STEP S8 that the key has been pressed and proceeds to STEP S9 so as to store data of the pressed key in the memory 18. Until it is confirmed in STEP S8 that the key has been pressed, the control section 15 keeps returning to STEP S7 and displaying the message urging the subject to press the key.

Similarly, in STEPS S10 to S12, the control section 15 urges the subject to enter his age, the subject enters his age, and the control section 15 stores the age data in the memory 18. In STEPS S13 to S15, the control section 15 urges the subject to enter his body height, the subject enters his body height, and the control section 15 stores the body height data in the memory 18.

Then, in STEP S16, it is determined which key has been pressed in STEP S8. In this case, since the subject is a normal male, it is determined to be "No", and the control section 15 proceeds to STEP S17.

In STEP S17, measurements are carried out after it is confirmed that the subject stands on the measuring section 2 with his toes in contact with the current supplying electrodes 5A and 6A and his heels in contact with the voltage measuring electrodes 5B and 6B. To measure a body weight, an output from the body weight sensor is taken into the control section 15, and the body weight is calculated in STEP S18. Meanwhile, to measure an impedance, a constant electric current is passed between the electrodes 5A and 6A from the constant current generating circuit 16, a voltage between the electrodes 5B and 6B is measured by the voltage measuring circuit 17, and the impedance is calculated based on the relationship between the current and the voltage in STEP S18. In STEP S18, the tare weight is subtracted from the measured body weight so as to determine the body weight of the subject; a body fat percentage is calculated from the impedance; a body fat mass is calculated by multiplying the body weight by the body fat percentage; a fat free mass is calculated by subtracting the body fat mass from the body weight; a total body water is calculated by multiplying the fat free mass by an average body water percentage which is 73.2%; and BMI (Body Mass Index) is calculated from the body height and the body weight.

Figure 5:
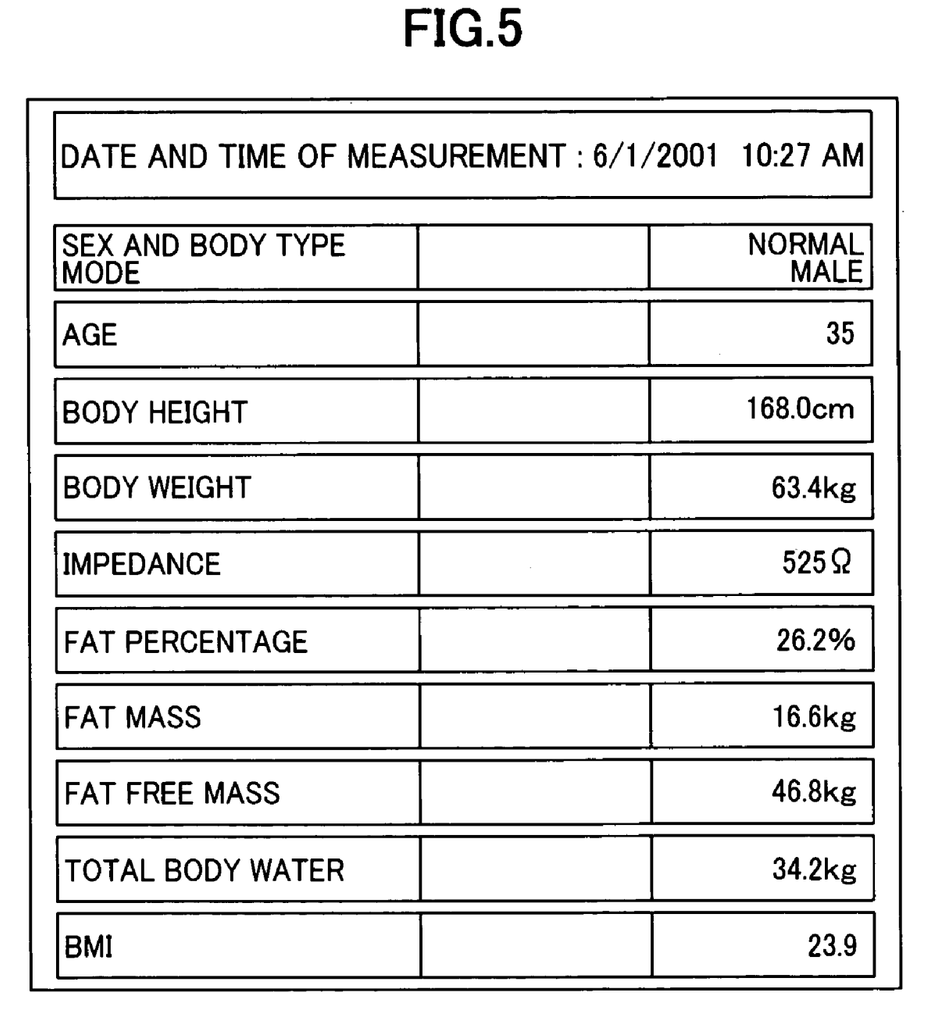
FIG. 5 is a diagram showing an example of printout in a non-maternity mode.

Then, the results of the calculations are not only displayed in the display section 8 but also printed out from the printing section 9 in STEP S19. FIG. 5 is an example of the printout. In addition to the date and time of the measurements, the entered personal data such as sex, a body type, age and a body height and the results of the measurements and calculations carried out in STEPS S17 and S18 are printed out.

After displaying and printing out the results, the control section 15 returns to STEP S4 and waits for the next input data.

Then, if the "maternity" key of FIG. 2 has been pressed in the above STEP S8, it is determined to be "Yes" in STEP S16, and the control section 15 proceeds to STEP S20. In STEP S20, the control section 15 displays in the display section 8 a message which urges the subject to enter an expected date of birth. STEPS S20 and S21 are repeated until the date is input by use of the numerical keypad in STEP S21.

Once the expected date of birth is entered, it is determined to be "Yes" in STEP S21, and the control section 15 calculates the present gestational weeks from the entered expected date of birth and date of measurements in STEP S22. Then, the control section 15 displays a message urging the subject to enter her body weight before pregnancy (in a non-pregnant state) in STEP S23 and proceeds to STEP S24.

When the body weight is entered by use of the numeric keypad, it is determined to be "Yes" in STEP S24, and the data is stored in the memory 18 in STEP S25.

In the case of maternity, processing in STEP S17 is the same as that of a non-maternity case. However, in the case of maternity, the following calculations are also performed in addition to the data calculations performed in STEP S18 of the non-maternity case.

Figure 6:
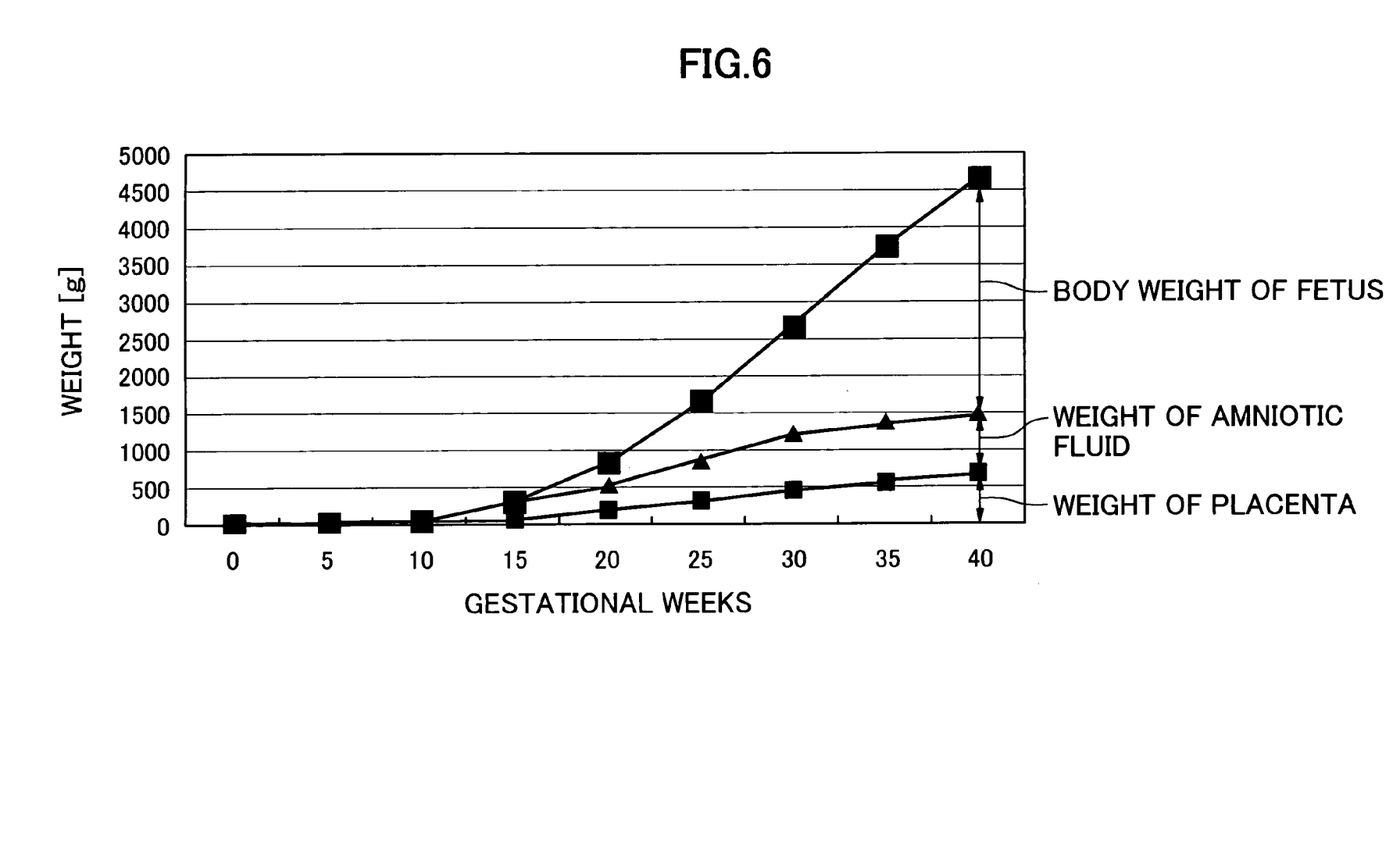
FIG. 6 is a diagram showing the relationship between the gestational weeks and the weight of fetal portion.

The body weight of fetus, the weight of amniotic fluid and the weight of placenta which correspond to the gestational weeks are read from the graph (whose data is stored in the memory 18) shown in FIG. 6. These are subtracted from the measured body weight from which the tare weight has already been subtracted so as to determine a body weight excluding the weight of the fetal portion. Based on this body weight, a body fat percentage, a body fat mass, a fat free mass, a total body water and the ratio of the total body water to the body fat mass (TBW/FAT) are calculated at the time of the measurement.

Then, the body weight in the non-pregnant state which has been input in STEP S24 is subtracted from the present body weight measured in STEP S17 so as to determine the amount of an increase in the body weight between the non-pregnant state and the time of the measurement. The present inventor has found that the ratios of the amounts of increases in body fat and body water between the non-pregnant state and the time of the measurement to the amount of an increase in the body weight are about 58% and about 29%, respectively. The present inventor has also found that these ratios remain unchanged from the $6^{th}$ week to the $16^{th}$ week of pregnancy and do not change even if the body weight changes due to morning sickness or some other reasons. Therefore, when the measurement is made between the $16^{th}$ week and the $16^{th}$ week of pregnancy, the amount of an increase in the body weight between the non-pregnant state and the present time is multiplied by these ratios so as to determine the amounts of increases in body fat and body water between the non-pregnant state and the time of the measurement, and the amount of an increase in body fat and the amount of an increase in body water are subtracted from the present body fat mass and total body water so as to determine a body fat mass and a total body water in the non-pregnant state in STEP S18.

The amount of an increase in body fat and the amount of an increase in body water between the non-pregnant state and the time of the measurement which are required to calculate the body fat mass and the total body water in the non-pregnant state can be calculated even in the middle or late stage of pregnancy, if a body fat mass and a total body water in the non-pregnant state which are determined by making a measurement at least once between the 6$^{th}$ week and the 16$^{th}$ week of pregnancy are stored in the memory 18.

Figure 7:
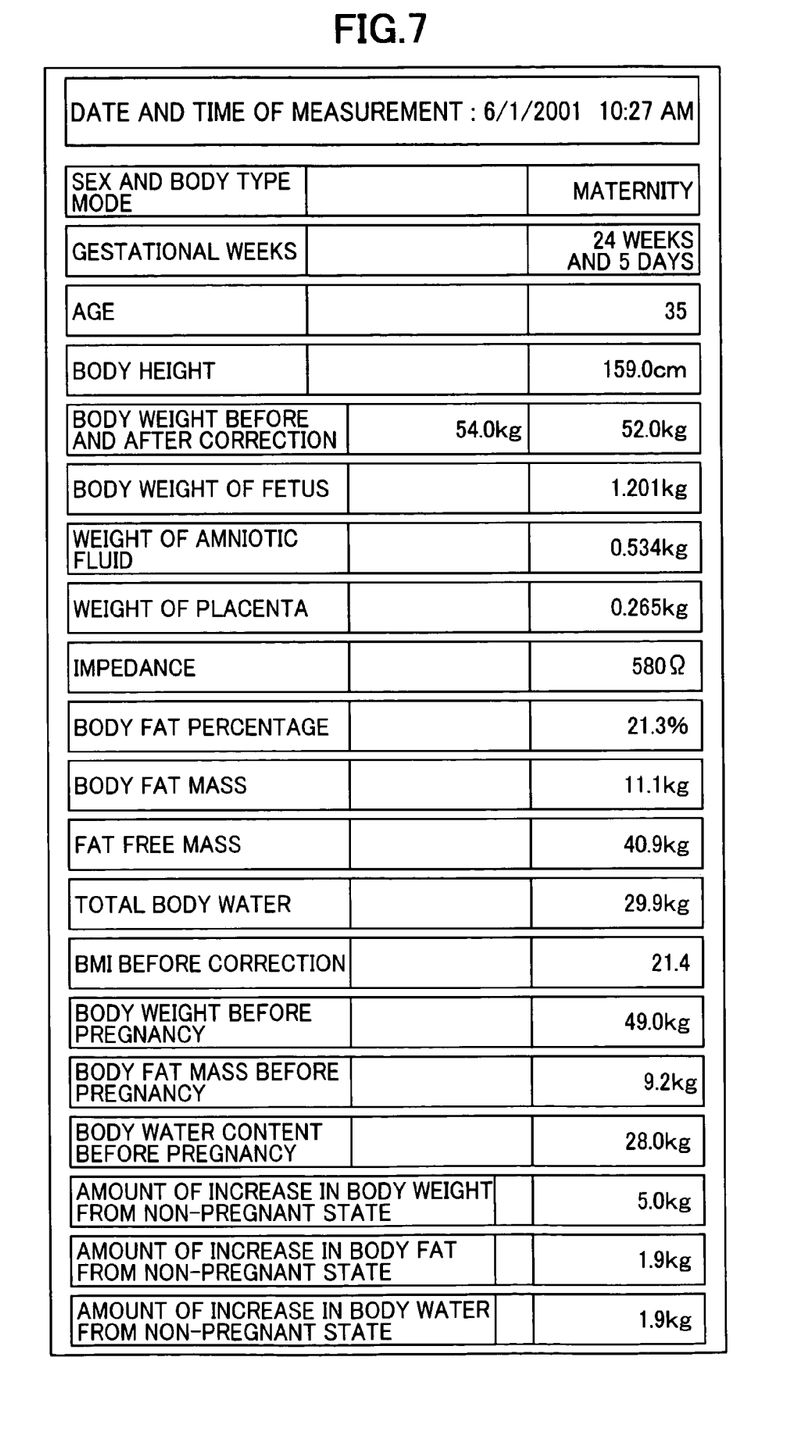
FIG. 7 is a diagram showing an example of printout in a maternity mode.

Then, the results are displayed in the display section 8 and printed out in the printing section 9 in STEP S19. An example of printout of the results of measurements made on 24 weeks plus 5 days of pregnancy in FIG. 7 is different from the example of FIG. 5 in that it further shows the gestational weeks, a body weight before correction (from which a tare weight has already been subtracted) including the weight of fetal portion and a body weight after correction excluding the weight of the fetal portion, the body weight of fetus, the weight of amniotic fluid, the weight of placenta, BMI before correction (non-corrected BMI) determined from the body weight (from which the tare weight has been subtracted) including the weight of the fetal portion and a body height, a body weight before pregnancy, a body fat mass before pregnancy, a total body water before pregnancy, and the amounts of increases in body weight, body fat and body water between the non-pregnant state and the time of the measurement. The non-corrected BMI is calculated and displayed or printed because the data is provided to a gynecologist who determines the developmental status of a fetus from the value of the non-corrected BMI.

Further, similarly, for the purpose of data provision, BMI before pregnancy may also be printed or displayed in addition to the example of printout shown in FIG. 7 or data displayed in the display section 8.

After completion of STEP S19 where the obtained results are displayed and printed, the control section 15 returns to STEP S4 and waits for the next input data.

Figure 8:
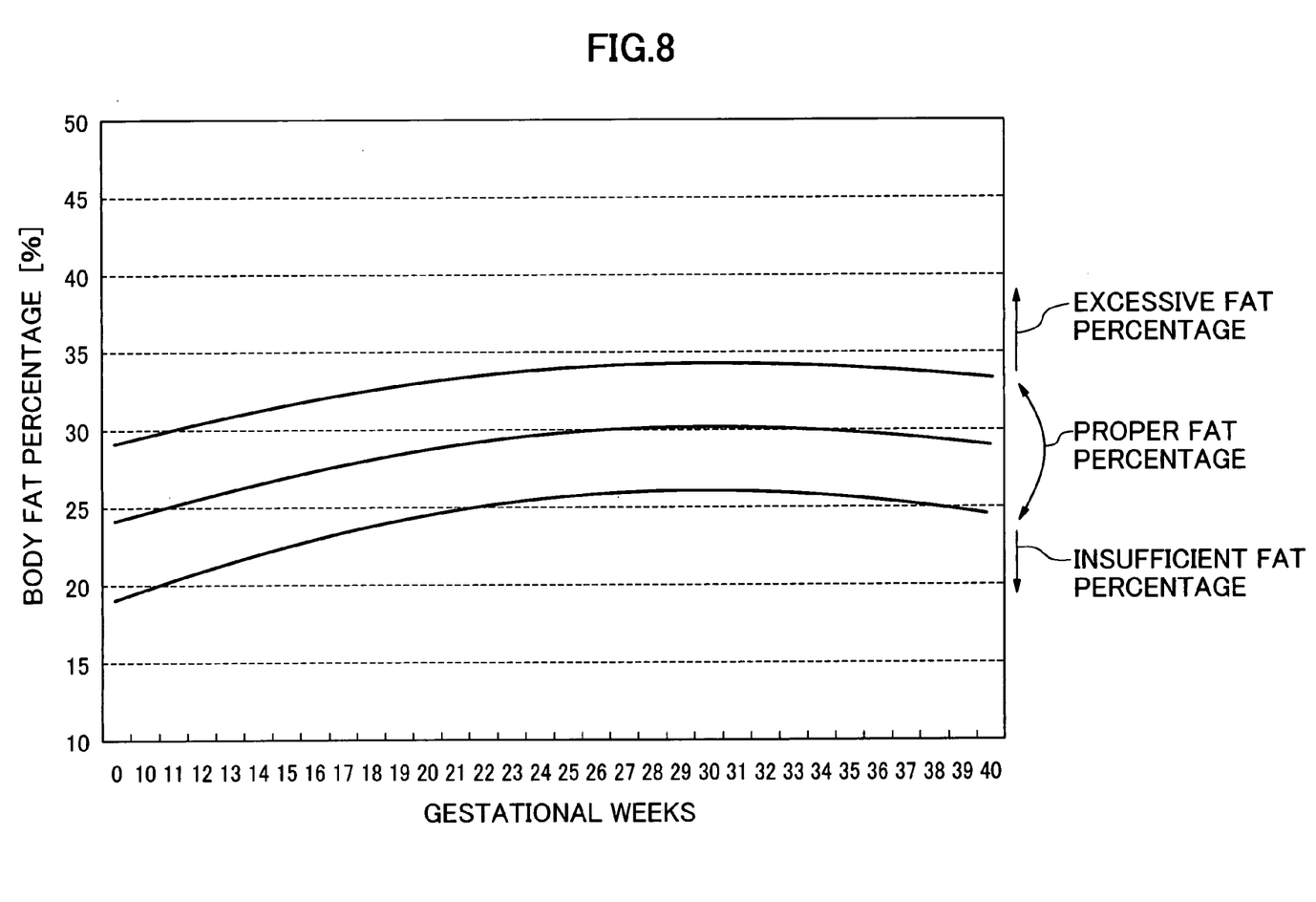
FIG. 8 is a diagram showing the relationship between the gestational weeks and a body fat percentage.

In the above maternity mode, the body fat percentage is displayed only in numerical values. However, since the relationship between the gestational weeks and a proper fat percentage has been found to be such that the fat percentage increases in the initial stage of pregnancy and slightly decreases in the late stage of pregnancy as shown in FIG. 8, the following can be achieved. That is, when data of this graph is stored in the memory 18, the body fat percentage is determined to be insufficient, proper and excessive according to the gestational weeks after the body fat percentage is calculated in STEP S18 and advice based on the determination is displayed or printed, pregnant women easily understand what to do with their present physical conditions.

Figure 9:
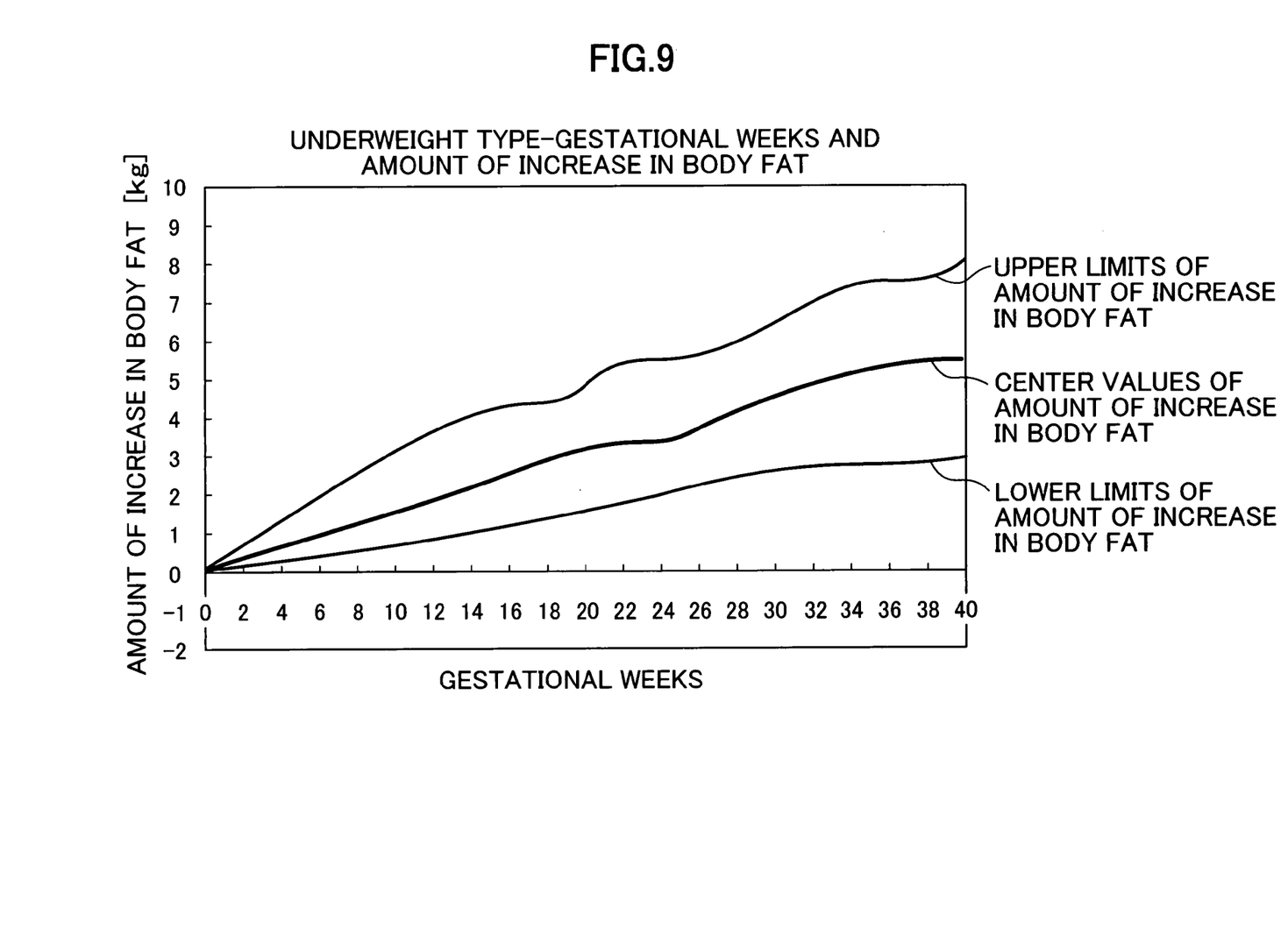
FIG. 9 is a diagram showing the relationship between the gestational weeks and the amount of an increase in body fat for a underweight female.
Figure 10:
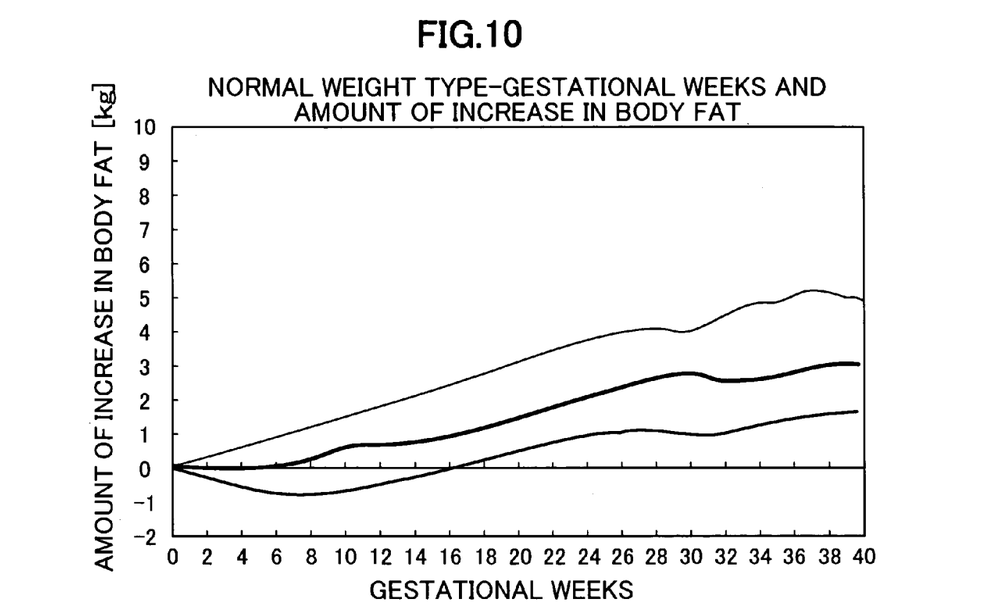
FIG. 10 is a diagram showing the relationship between the gestational weeks and the amount of an increase in body fat for a normal female.
Figure 11:
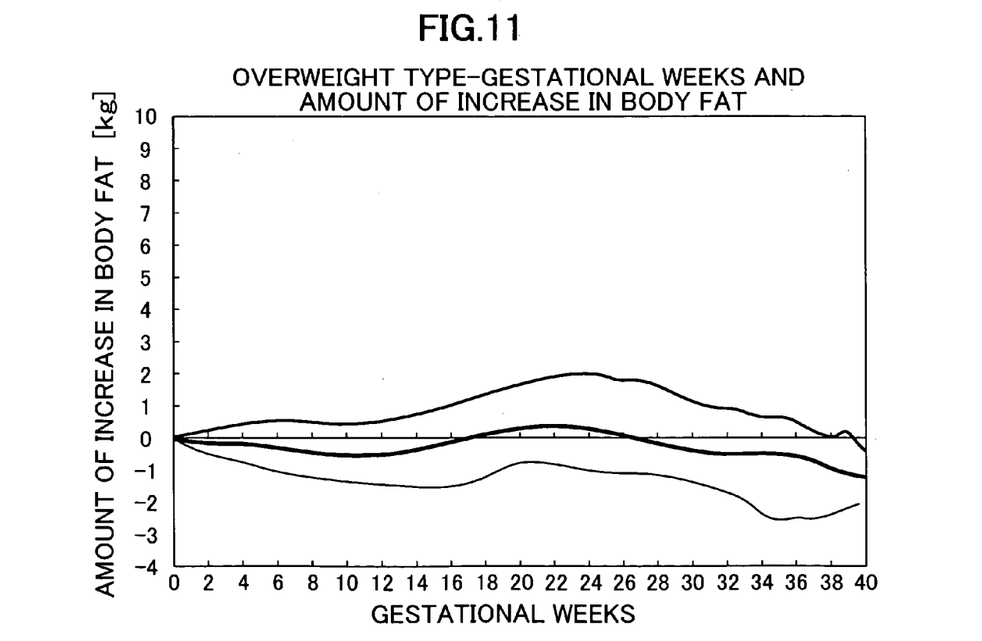
FIG. 11 is a diagram showing the relationship between the gestational weeks and the amount of an increase in body fat for an overweight female.

Further, in the above maternity mode, a determination such as "insufficient", "proper" or "excessive" is made and advice is given based on the relationship between the gestational weeks and the body fat percentage in FIG. 8. Alternatively, it is also possible that a determination such as "insufficient", "proper" or "excessive" is made and advice is given as in the case of FIG. 8, based on the relationship between the gestational weeks and the amount of an increase in body fat from the non-pregnant state. In this case, proper ranges differ as shown in FIGS. 9, 10 and 11, depending on whether the body type in the non-pregnant state is a underweight type (BMI is less than 18), a normal type (BMI is 18 to 24) or an overweight type (BMI is more than 24). In these drawings, the middle graph represents center values of a proper amount of an increase in body fat, the upper graph represents upper limits of the proper amount of an increase in body fat, and the lower graph represents lower limits of the proper amount of an increase in body fat. Consequently, BMI in the non-pregnant state is calculated in STEP S18 of FIG. 4, and when the amount of an increase in body fat which exceeds the upper graph is measured, advice such as "The amount of an increase in body fat is excessive. A desirable dietary menu is as follows." can be displayed in the display section 8 or printed out from the printing section 9.

Further, in the present embodiment, the body weight of fetus, the weight of amniotic fluid and the weight of placenta are estimated according to the gestational weeks in FIG. 6 and input automatically. Alternatively, the data may be input in numerical values by use of the numeric keypad 14 for each measurement.

Further, in the above embodiment, the results of calculations are displayed or printed. However, it is also possible that past records are read from the memory 18 and a graph of the results of calculations is displayed on the graphs of FIGS. 8, 9, 10 and 11 so as to display changes in the past.

The present invention is a body composition management apparatus for a pregnant woman which measures body fat or body water by a bioelectrical impedance method, the apparatus comprising:
first input means,
second input means,
measurement means,
first computation means, and
second computation means,
wherein
the first input means inputs personal data of a pregnant woman such as a body height and a body weight,
the second input means inputs the gestational weeks,
the measurement means measures the bioelectrical impedance of the pregnant woman,
the first computation means computes a body fat mass or a total body water from the personal data and the impedance, and
the second computation means computes a body fat mass or total body water in a non-pregnant state from the computed body fat mass or total body water and the amount of an increase in body weight from the non-pregnant state. The apparatus can determine the body fat mass or total body water in the non-pregnant state easily even if a subject does not remember the body fat mass or total body water in the non-pregnant state and can manage a body composition of a pregnant woman such as a body fat mass or a total body water.

Further, the second input means can determine the gestational weeks easily by taking in an expected date of birth.

Further, the present invention can measure the body fat percentage of a pregnant woman accurately by taking in the weight of fetal portion which has been determined from the gestational weeks.

What is claimed is:

1. A body composition management apparatus for a pregnant woman for measuring body fat or body water by a bioelectrical impedance method, the apparatus comprising:
    first input means for inputting personal data of a pregnant woman such as a body height and a body weight,
    second input means for inputting gestational weeks,
    measurement means for measuring the bioelectrical impedance of the pregnant woman,
    first computation means for computing a body fat mass or a total body water from the personal data and the bioelectrical impedance, and
    second computation means for computing a body fat mass or total body water in a non-pregnant state from the body fat mass or total body water computed by the first computation means, and the amount of an increase in body weight from the non-pregnant state.

2. The apparatus of claim 1, wherein the second input means is for taking in an expected date of birth so as to determine the gestational weeks.

3. The apparatus of claim 1 or 2, wherein the apparatus is adapted to prepare health management data from a change in the body fat mass or total body water between the non-pregnant state and the time of the measurement.

* * * * *